United States Patent [19]

Appelgren et al.

[11] Patent Number: 4,937,080

[45] Date of Patent: Jun. 26, 1990

[54] GRANULAR PRODUCT (I)

[75] Inventors: Curt H. Appelgren, Kungsbacka; Ulf A. Odda, Gothenburg, both of Sweden

[73] Assignee: Lejus Medical Aktiebolag, Molndal, Sweden

[21] Appl. No.: 238,612

[22] Filed: Aug. 31, 1988

[30] Foreign Application Priority Data

Aug. 31, 1987 [SE] Sweden ................................ 8703358

[51] Int. Cl.$^5$ .............................................. A61K 9/16
[52] U.S. Cl. ................................. 424/490; 424/403; 424/468; 424/469; 424/470; 424/472; 424/493; 427/3; 71/28; 71/64.07
[58] Field of Search ............... 424/490, 468, 469, 470, 424/472, 403, 493; 427/3; 71/28, 64.07

[56] References Cited

U.S. PATENT DOCUMENTS

| | | | |
|---|---|---|---|
| 2,887,438 | 5/1959 | Cooper | 424/472 |
| 4,439,453 | 3/1984 | Vogel | 424/493 |
| 4,465,660 | 8/1984 | David | 424/468 |
| 4,716,041 | 12/1987 | Kjornaes | 424/469 |

*Primary Examiner*—Thurman K. Page
*Attorney, Agent, or Firm*—Burns, Doane, Swecker & Mathis

[57] ABSTRACT

The present invention relates to a granular product comprised of a solid product which has been provided with a coating of a melt of itself, as well as a process for the preparation of the granular product.

5 Claims, No Drawings

GRANULAR PRODUCT (I)

TECHNICAL FIELD

The present invention relates to granular products, and a process for preparing the same.

The object of the present invention is to obtain granular products, which essentially consists of one, pure product.

BACKGROUND OF THE INVENTION

Powder that is to be tabletted as a general rule does not have the flowing characteristics that is wanted but are cohesive and thus it is common that the powder is converted into a granulate prior to tabletting.

At the production of the granulate, the powder is provided with a solvent, optionally containing a binding agent so as to form a semi moist mass, which is then formed into agglomerates and is dried to granules, or if a suitable size of the agglomerate is obtained directly, is immediately dried to a suitable particle size which varies dependent on the intended use. Optionally, the granulate has to be crushed to obtain the right particle size and particle size distribution. The size may vary from some 100 μm to 1.5 mm in diameter.

All products are, however, not suited for a treatment using a solvent and often an inert carrier has to be added to obtain a suitable granulate.

One way of obtaining a solvent-free granulate is to add another powder having good binding properties, to compress the pulverulent mixture into tablets or briquettes and then to crush these into a suitable particle/-granulate size.

It has also for several reasons, such as a desire to get rid of unnecessary additions, been desirable to obtain highly concentrated products, and others, have raised demands for pure granulates, i.e. granulates which contain the desired substance/product, only, or at least contain essentially, i.e., 80-100% of the product desired.

DESCRIPTION OF THE PRESENT INVENTION

It has now surprisingly been shown possible to be able to solve this problem by means of the present invention which is characterized in that the solid substance to be granulated is coated with a melt of itself, and then is rapidly cooled.

Further characteristics are evident from the accompanying claims.

The coating using a melt of itself shall thereby be carried out under such conditions that the temperature of the solid product is not considerably increased, i.e., does not increase more than 5°-10° C. for a long time period, i.e., more than 30 sec.

Momentarily, the temperature increase might be greater, but due to a rapid treatment the granules obtained are chilled in such a way that the increase of the temperature during at most 30 sec. extends to 5°-10° C. only.

The relation between solid material: melt is 70-95:-30-5. The melt has in general a temperature of 10°-20° C. above the melting point of the product.

Substances/products which have turned out to be particularly suited for a granulation with itself are ibuprofen, ketoprofen, pirprofen, phenoprofen, fluorbiprofen, naproxene (pharmaceutically active compounds), xylose, xylitol, sorbitol, (three known sweetening agents). Other products that might be coated with itself are urea, acetylcysteine, dextrane. Products which can be coated with itself have a melting point in the range of 35°-200° C.

Ibuprofen has turned out to be particularly suitable for a granulation with itself, as the granulate obtained can be directly compressed into therapeutically active tablets using a minimal addition of disintegration and lubricating agents, whereby one obtains a tablet having suitable release properties. Ibuprofen is a therapeutically active compound which shall be administered in very large doses per day (1.2 g or more) and thus it is desirable that as much as possible of the tablet/dose form consists of pure active substance. Pulverulent, crystalline ibuprofen can not be readily compressed directly due to lack of flowing properties (EP-A1-0 120 587).

It shall be noted that a coating with a melted or softened material is previously known. Thus it is known to introduce, into a fluid bed apparatus, a powder and a wax and to obtain a wax coating by increasing the temperature of the air used to be blown through the bed. It is also known to add a powder to a melt present in a vessel provided with a jacket, to allow the melt to stiffen, and to crush it to a suitable size. These processes, however, leads to high increases of temperature in the material to be treated for a long time.

The coating of the solid product with itself can be done in an apparatus described in SE-C-7903053-2 and in such a way as described in SE-A-8500487-7.

The apparatus according to SE-C-7903053-2 comprises a mixing house provided with a cover. Within the housing a disc is arranged which disc consists of an upper disc and a lower disc, which disc is rotatably mounted around a shaft by means of a bearing. Between the upper and the lower discs there is a hollow space which is connected to the upper side of the upper disc via an annular slot consisting of two parts which both take the shape of a circumferential surface of a cut cone with its point directed downwardly. The upper disc has blades cut on its upper side and optionally cut, or mounted blades on its side underneath. Between the blades spaces exist which are intended to receive particles to be coated while said space optionally being divided into compartments by means of said blades is intended to receive the melt which is to be used for coating. The lower disc is provided with an edge extending around it close to the opening of the slot. At its periphery the lower disc is provided with blades for throwing out the final product via a diffusor and an outlet. The cover is provided with a compartment placed above the centre of the disc which compartment is arranged to receive the particulate solid material for a further transport thereof to said above mentioned spaces between the blades. The particulate solid material is fed to the compartment of the cover by means of a transporting device, e.g. a feeding screw. The liquid phase is fed to the space via a tube.

At the coating operation according to SAE-A-8700487-7 the discs are rotated within the housing around the shaft with a revolving speed of between 1000 to 500 rpm. A suitable peripheral speed using a disc diameter of 300 mm is 1500 to 5000 m per minute whereby the lower speed is used for embedding/agglomeration and the higher for coating. The coating melt is thereby fed to the apparatus via the tube to the hollow space between the upper and the lower discs. The tube is thereby provided with heating means in order to keep the material in melted, liquid form. By means of the centripetal force and the blades the melt is thrown outwardly through the slot and further through the outer slot. The melt hereby takes the form of a membrane which extends outwardly all the time simultaneously as it becomes thinner. When the melt leaves the outer slot the membrane is torn up into very small droplets when it leaves the edge, whereby a mist curtain of droplets having a microscopic size is formed. Simultaneously with the addition of melt through the tube, a particulate material is added by means of the transporting device to the compartments and further on to the spaces on the upper side of the upper disc. From there the particulate material is thrown, by means of the centripetal force, and the blades, outwardly towards the periphery of the upper disc, simultaneously as it is deagglomerated into primary particles which meet with and pass the mist curtain at the edge. The particles hereby obtain a surface coating of the melt and are further thrown outwardly to the blades arranged at the periphery of the lower disc, which blades throw the product out off the apparatus via the diffusor and the outlet. Depending on the number of blades their height and the through-put, which can be varied using the outlet area, one can get an agglomeration of the particles, or get the particles out as separate sole, coated particles. The granulate obtained is directly chilled with air during the throwing out thereof and is further chilled at a following separation in a cyclone or the like.

EXAMPLE 1

700 g of ibuprofen were introduced as a powder in an apparatus according to the above, whereby a melt having a temperature of 90° C. was introduced. The melt consisted of 300 g of ibuprofen, which in the contacting zone between powder and melt coated the powder with melt, whereby a 100% pure ibuprofen in granular form was obtained. The particle size of the product obtained was 200 μm–1400 μm.

The ibuprofen granulate, 92.5%, mixed with 5% of Avicel (microcrystalline cellulose), 2.0% of Ac-Di-Sol (crosslinked sodium carboxymethyl cellulose), 0.5% Mg-stearate was introduced into a tabletting machine, whereby tablets were able to be compressed directly. The tavblets had a weight of 400 mg per piece. The disintegration time was less than 60 s. The release rate according to USP XXI, pebble method, 100 rpm, phosphate buffer pH 6.2 was $T_{50}<4$ min. A pure ibuprofen granulate had a Hausner ratio of 1.23 and an angle of repose of 57.7°. The composition used for tabletting purposes above had a Hausner ratio of 1.13 and an angle of repose of 49.8°.

EXAMPLE 2

Crystalline xylitol, 700 g, were treated in accordance with example 1 above, whereby xylitol in solid state met a melt of xylitol, 300 g, having a temperature of 20° above the melting point of the xylitol, i.e., about 100° C.

The granulate of pure xylitol as obtained could be compressed directly without any addition of tabletting aiding agents. The xylitol obtained is an excellent basis for chewing tablets.

EXAMPLE 3

Sorbitol was treated in accordance with Ex. 1 above, whereby a direct compressible granulate was obtained. The temperature of the melt was 90°–95° C.

We claim:

1. A process for the preparation of granular product comprising coating a solid product with a melt of said solid product having a melting point of 35°–200° C. and having a temperature exceeding the melting point of said solid product by 10°–20° C., such that the temperature of the solid product during the coating with the melt is allowed to increase only up to 10° C., and whereby the granular product has a weight ratio of the solid product to the coating of 70–95:5–30.

2. A process for the preparation of granular product comprising coating ibuprofen with a melt of ibuprofen having a temperature exceeding the melting point of ibuprofen by 10°–20° C., such that the temperature of ibuprofen during the coating with the melt is allowed to increase only up to 10° C., and whereby the granular product has a weight ratio of ibuprofen to the coating of 70–95:5–30.

3. The process of claim 1 wherein the solid material is xylitol.

4. The process of claim 1 wherein the solid material is sorbitol.

5. The process of claim 1 wherein the solid material is urea.

* * * * *